United States Patent [19]

Huellmann et al.

[11] Patent Number: 5,359,122
[45] Date of Patent: Oct. 25, 1994

[54] PREPARATION OF 3-ARYLACRYLIC ACIDS AND THEIR DERIVATIVES

[75] Inventors: Michael Huellmann, Bensheim; Josef Gnad, Ludwigshafen; Rainer Becker, Bad Duerkhaim, all of Fed. Rep. of Germany

[73] Assignee: BASF Aktiengesellschaft, Ludwigshafen, Fed. Rep. of Germany

[21] Appl. No.: 193,872

[22] Filed: Feb. 8, 1994

Related U.S. Application Data

[63] Continuation of Ser. No. 771,184, Oct. 4, 1991, abandoned.

[30] Foreign Application Priority Data

Dec. 13, 1990 [DE] Fed. Rep. of Germany ....... 4039782

[51] Int. Cl.$^5$ .......................................... C07C 69/734
[52] U.S. Cl. ..................................... 560/20; 560/21; 560/55; 560/100; 560/104; 562/490; 562/497; 562/493; 562/495
[58] Field of Search ............... 562/490, 492, 493, 495; 560/55, 20, 21, 100, 104

[56] References Cited

U.S. PATENT DOCUMENTS

| | | | |
|---|---|---|---|
| 4,609,756 | 9/1986 | Dorlars et al. ................. | 562/495 |
| 4,785,133 | 11/1988 | Raynolds et al. . | |
| 4,827,021 | 5/1989 | Jones et al. . | |

FOREIGN PATENT DOCUMENTS

| | | |
|---|---|---|
| 3437634 | 4/1986 | Fed. Rep. of Germany . |
| 1023176 | 3/1966 | United Kingdom . |

OTHER PUBLICATIONS

Journal of Organometallic Chemistry, 234 (1982), pp. 73–83. Eckhart K. G. Schmidt et al: "Synthese, Eigenschaften Und Carbonyl–Insertions–Reaktionen Von Tetra . . . ".
Frantisek Sorm a Jiri Smrt, "Reakce Ketenu S Acetaly Aldehydu A S Orthomravencanem Ethylnatym" pp. 413–417, 1953.

Primary Examiner—Marianne M. Cintins
Assistant Examiner—Keith MacMillan
Attorney, Agent, or Firm—Oblon, Spivak, McClelland, Maier & Neustadt

[57] ABSTRACT

The preparation of 3-arylacrylic acids and their derivatives I

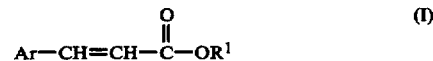

where
Ar is aryl which can additionally have substituents which do not react with ketene and are stable under the conditions of the reaction described below, and
$R^1$ is hydrogen, an alkali metal, an alkaline earth metal, ammonium or $C_1$–$C_{20}$-alkyl, comprises a first stage in which a dialkyl acetal of an aromatic aldehyde of the formula II

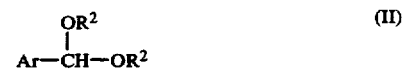

where $R^2$ is $C_1$–$C_4$-alkyl, is reacted with ketene of the formula $CH_2=C=O$ in the presence of catalytic amounts of a protic or Lewis acid to give a 3-arylpropionic acid derivative of the formula III

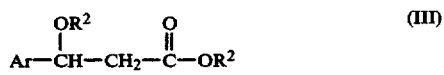

and a second stage in which this intermediate III is reacted in the presence of acid or base and, in the case where $R^1$ is $C_1$–$C_{20}$-alkyl, additionally with a $C_1$–$C_{20}$-alkanol to give the final product I.

5 Claims, No Drawings

PREPARATION OF 3-ARYLACRYLIC ACIDS AND THEIR DERIVATIVES

This application is a continuation application Ser. No. 07/771,184, filed on Oct. 4, 1991, now abandoned.

The present invention relates to an improved process for preparing 3-arylacrylic acids and their derivatives of the formula I $$Ar-CH=CH-\overset{O}{\underset{\|}{C}}-OR^1 \quad (I)$$

where

Ar is aryl which can additionally have substituents which do not react with ketene and are stable under the conditions of the process according to the invention, and $R^1$ is hydrogen, an alkali metal, an alkaline earth metal, ammonium or $C_1$-$C_{20}$-alkyl.

The present invention also relates to the use of the compounds I prepared by the process according to the invention as sunscreen agents for cosmetic preparations.

The processes to date for preparing compounds I are predominantly based on base-catalyzed aldol reactions, for example starting from aromatic aldehydes and acetic esters. The disadvantages of this method are the relatively large quantity of salt produced in the working up and the risk of the formation of a large number of by-products.

Another known method for synthesizing compounds I is based on the addition of ketene onto aromatic aldehyde. For example, the method in DE-A 34 37 634 (1) uses catalytic amounts of iron and/or zinc salts of mono- or dicarboxylic acids, although an elaborate depolymerization is necessary to form the free cinnamic acids. The yields and the purity of the products resulting from the process described in (1) are, however, still in need of improvement.

The preparation of ethyl 3-ethoxy-3-phenylpropionate from benzaldehyde diethyl acetal by reaction with ketene in the presence of 0.2 mol of boron trifluoride etherate at 0° C. is described in Chem. Listy 47 (1953), 413–417, (2) (see Table 1). The yield is only 32%.

The 3-arylpropionic acid derivatives III which occur as intermediates in the process according to the invention are known, e.g. methyl 3-methoxy-3-phenylpropionate and its p-methyl, p-methoxy, p-chloro and p-fluoro derivative from J. Organomet. Chem. 234 (1982), 73–83, (3).

It is an object of the present invention to provide a process for preparing the compounds I which is improved in respect of economics, yield and purity of the product.

We have found that this object is achieved by an improved process for preparing 3-arylacrylic acids and their derivatives of the formula I $$Ar-CH=CH-\overset{O}{\underset{\|}{C}}-OR^1 \quad (I)$$

where

Ar is aryl which can additionally have substituents which do not react with ketene and are stable under the conditions of the process according to the invention, and $R^1$ is hydrogen, an alkali metal, an alkaline earth metal, ammonium or $C_1$-$C_{20}$-alkyl, which comprises a first stage in which a dialkyl acetal of an aromatic aldehyde of the formula II $$Ar-\overset{OR^2}{\underset{|}{CH}}-OR^2 \quad (II)$$

where $R^2$ is $C_1$-$C_4$-alkyl, is reacted with ketene of the formula $CH_2=C=O$ in the presence of catalytic amounts of a protic or Lewis acid to give a 3-arylpropionic acid derivative of the formula III $$Ar-\overset{OR^2}{\underset{|}{CH}}-CH_2-\overset{O}{\underset{\|}{C}}-OR^2 \quad (III)$$

and a second stage in which this intermediate III is reacted in the presence of acid or base and, in the case where $R^1$ is $C_1$-$C_{20}$-alkyl, additionally with a $C_1$-$C_{20}$-alkanol to give the final product I.

In a preferred embodiment, Ar is phenyl, biphenylyl or naphthyl, each of which can be substituted by one to three $C_1$-$C_4$-alkyl groups, $C_1$-$C_4$-alkoxy groups, hydroxyl groups, phenoxy groups, amino groups which can be mono- or disubstituted by $C_1$-$C_4$-alkyl, halogen atoms, nitro groups or a methylenedioxy group, it being possible for the substituents to be identical or different.

Examples of Ar are:
phenyl,
o-, m- or p-tolyl,
o-, m- or p-ethylphenyl,
o-, m- or p-propylphenyl,
m- or p-cumyl,
o-, m- or p-butylphenyl,
m- or p-iso-butylphenyl,
m- or p-sec-butylphenyl,
m- or p-tert-butylphenyl,
2,3-, 2,4-, 2,5-, 2,6-, 3,4- or 3,5-dimethylphenyl, mesityl,
o-, m- or p-methoxyphenyl,
o-, m- or p-ethoxyphenyl,
o-, m- or p-propoxyphenyl,
m- or p-iso-propoxyphenyl,
o-, m- or p-butoxyphenyl,
m- or p-iso-butoxyphenyl,
m- or p-sec-butoxyphenyl,
m- or p-tert-butoxyphenyl,
2,3-, 2,4-, 2,5-, 2,6-, 3,4- or 3,5-dimethoxyphenyl,
o-, m- or p-hydroxyphenyl,
2,3-, 2,4-, 2,5-, 2,6-, 3,4- or 3,5-dihydroxyphenyl,
3-hydroxy-4-methoxyphenyl,
m- or p-phenoxyphenyl,
o-, m- or p-aminophenyl,
o-, m- or p-(N-methylamino)phenyl,
o-, m- or p-(N,N-dimethylamino)phenyl,
o-, m- or p-fluorophenyl,
o-, m- or p-chlorophenyl,
2,4-dichlorophenyl,
o-, m- or p-bromophenyl,
o-, m- or p-nitrophenyl,
2,3- or 3,4-methylenedioxyphenyl,
2-, 3- or 4-biphenylyl and
α- or β-naphthyl.

$C_1$-$C_4$-Alkoxyphenyl is particularly preferred, especially when the alkoxy is in the para position on the phenyl.

If R¹ is hydrogen, an alkali metal, especially sodium or potassium, an alkaline earth metal, e.g. calcium or magnesia, or ammonium, the compounds I are the free 3-arylacrylic acids or their salts. If R¹ is $C_1-C_{20}$-alkyl, the compounds are esters of 3-arylacrylic acids. Of these, hydrogen and, especially, $C_1-C_{20}$-alkyl are preferred.

Examples of straight-chain or branched $C_1-C_{20}$-alkyl are methyl, ethyl, n-propyl, iso-propyl, n-butyl, tert-butyl, n-pentyl, n-hexyl, n-heptyl, n-octyl, 2-ethylhexyl, n-nonyl, iso-nonyl, n-decyl, n-undecyl, n-dodecyl, n-tridecyl, iso-tridecyl, n-tetradecyl, n-hexadecyl, n-octadecyl and n-eicosyl. Of these, straight-chain or branched $C_1-C_{16}$-alkyl, especially straight-chain or branched $C_8-C_{12}$-alkyl, are preferred. Straight-chain or branched $C_8$-alkyl is of particular interest.

In the first stage, a dialkyl acetal of an aromatic aldehyde II where R² can be $C_1-C_4$-alkyl, e.g. methyl, ethyl, n-propyl, iso-propyl, n-butyl, 1,2-ethylene or 1,3-propylene, with methyl and ethyl being preferred, is reacted with ketene, normally at from $-20°$ to $80°$ C., in particular $-10°$ to $50°$ C. It is expedient to employ from 0.8 to 1.2 mol, preferably 0.9 to 1.1 mol, especially 0.94 to 1.06 mol, of ketene per mol II.

The reaction is preferably carried out without solvent but can also be carried out in an inert nonprotonate organic solvent. Suitable solvents are hydrocarbons, e.g. pentane, hexane, heptane, octane, cyclohexane, toluene, xylene or mixtures thereof, or ethers, e.g. diethyl ether, methyl tert-butyl ether or tetrahydrofuran, or mixtures thereof.

The reaction of II with ketene is carried out in the presence of catalytic amounts of a protic acid, e.g. sulfuric acid, hydrochloric acid, acetic acid, formic acid or p-toluenesulfonic acid, or of a Lewis acid, e.g. a boron trihalide dialkyl etherate such as boron trifluoride dimethyl etherate or boron trifluoride diethyl etherate, tetraalkoxytitanium or a zinc carboxylate. By catalytic amounts are meant in the case of protic acids normally from 0.001 to 1 mol % per mol of II, and in the case of Lewis acids nominally from 0.1 to 10 mol % per mol of II.

The reaction is expediently carried out in such a way that a solution of the protic acid or Lewis acid in the starting compound II, with or without addition of organic solvent, is adjusted to the reaction temperature and the ketene is passed in, preferably under atmospheric pressure. The ketene usually reacts immediately. Since the reactions are usually highly exothermic, it is advisable to cool the mixture. Traces of byproducts often make the reaction mixture intensely colored, for example violet, but this has no adverse effects subsequently.

It is usually easy to isolate the intermediate III in pure forth, for example by distillation under reduced pressure. However, in a preferred embodiment, the intermediate III is not isolated and the second stage of the reaction is carried out with the crude product from the first stage.

In the second stage, the intermediate III is reacted in the presence of acid, normally a protic acid, e.g. sulfuric acid, hydrochloric acid, acetic acid, formic acid or p-toluenesulfonic acid, or base, e.g. alkali metal or alkaline earth metal hydroxide such as sodium hydroxide, potassium hydroxide or calcium hydroxide or alkali metal or alkaline earth metal alcoholate such as sodium methylate, sodium ethylate or potassium tert-butylate. Catalytic amounts thereof are usually sufficient for such hydrolyses and eliminations, but if it is wished to obtain, for example, the alkali metal or alkaline earth metal salt of a 3-arylacrylic acid I, stoichiometric amounts of the appropriate base are necessary.

If $C_1-C_{20}$-alkyl 3-arylacrylates are prepared as 3-arylacrylic acid derivatives I, it is necessary to employ $C_1-C_{20}$-alkanol in addition. The selection of the $C_1-C_{20}$-alkyl in these alkanols is based on the same criteria as that of R¹. This reaction is a transesterification, i.e. replacement of the R² alkyl group by an R¹ alkyl group, with simultaneous elimination of a second molecule of R²—OH. The $C_1-C_{20}$-alkanol is employed in equimolar amount or, preferably, in excess, for example from 1.1 to 10 mol per mol III, in particular from 2 to 10 mol per mol III.

The second stage is usually carried out at elevated temperatures, for example at from $70°$ to $250°$ C., in particular at from $100°$ to $200°$ C. The elimination of one equivalent of R²—OH starts at from $70°$ to $100°$ C., the hydrolysis for transesterification takes place at from $150°$ to $250°$ C. with elimination of a second equivalent of R²—OH. An excess of $C_1-C_{20}$-alkanol is normally removed by distillation. The crude product obtained in this way is expediently purified by conventional methods, for example by distillation under reduced pressure.

If Ar has substituents which have been protonated by acid treatment during the process according to the invention or have formed an adduct with a Lewis acid, or substituents which have been anionized by base treatment during the process according to the invention, the substituents can easily be returned to the original form by treatment with an appropriate amount of a suitable base or acid.

The present invention also relates to the two stages in the reaction as individual processes. Thus, the invention relates to a process for preparing 3-arylpropionic acid derivatives of the formula IIIa

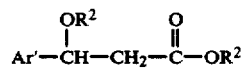

where
Ar' is aryl which has substituents which do not react with ketene and are stable under the conditions of the process according to the invention, or is unsubstituted biphenylyl or naphthyl, and
R² has the abovementioned meanings,
which comprises reacting a dialkyl acetal of an aromatic aldehyde of the formula IIa

with ketene of the formula $CH_2=C=O$ in the presence of catalytic amounts of a protic or Lewis acid.

In a preferred embodiment, the substituents are the same as for the Ar group.

The corresponding process for reacting unsubstituted benzaldehyde dialkyl acetal with ketene is disclosed in (2). However, the very low yield of 32% when R²=ethyl suggested that this process generally does not take place with good yields.

The invention also relates to a process for preparing 3-arylacrylic acids and their derivatives I, which comprises reacting a 3-arylpropionic acid derivative III in the presence of acid or base and, in the case where $R^1$ is $C_1$–$C_{20}$-alkyl, additionally with a $C_1$–$C_{20}$-alkanol.

The 3-arylacrylic acids and their derivatives I prepared by the process according to the invention are mainly used as sunscreen agents for cosmetic preparations.

The process according to the invention provides a straightforward and economic way for preparing 3-arylacrylic acids and their derivatives I, especially since the starting compound II can easily be obtained by electrochemical oxidation of the methyl group in the corresponding methylaromatic compound. The aromatic aldehydes employed as starting compounds in the process disclosed in (1) are, by contrast, obtainable only by elaborate syntheses, for example by the oxidation of methylaromatic compounds, for example toluene derivatives, with chromic acid, which is, moreover, toxicologically objectionable.

The process according to the invention provides the compounds I in good yields and free of large amounts of interfering byproducts so that subsequent purification operations are straightforward. In particular, excellent space-time yields are obtained in solvent-free reactions.

It is even possible, with appropriate choice of the catalyst systems in the two stages of the reaction, to prepare other economically useful products at the same time as the compounds I. For example, if a boron trifluoride dialkyl etherate is used as catalyst in the first stage, and a sodium alcoholate is used as catalyst in the second stage, it is possible additionally to obtain sodium fluoride and a trialkyl borate from the process.

EXAMPLE

Preparation of 2-ethylhexyl p-methoxycinnamate 89 g (2.12 mol) of ketene were passed, over the course of 3 hours, into a mixture of 364 g (2.0 mol) of p-methoxybenzaldehyde dimethyl acetal and 10 ml (0.11 mol) of boron trifluoride dimethyl etherate at about 15° C., cooling the reaction mixture during this with ice-water. The solution became deep violet on addition of ketene. The result after introduction of ketene was complete was 458 g of a violet liquid which, according to gas chromatography, contained 76.1% by weight of methyl 3-methoxy-3-(p-methoxyphenyl)propionate.

40 g of 30% by weight methanolic sodium methylate solution were added to this liquid, resulting in a pH of about 10 and a change in color from violet to yellowish brown. After addition of 780 g (6.0 mol) of 2-ethylhexanol, the mixture was slowly heated to 150° to 180° C., with 151 g of a liquid which was mainly composed of methanol distilling out over the course of about 1 hour. Excess 2-ethylhexanol was removed by distillation, and the residue was purified by distillation under about 1 mbar. 436 g of the title compound with a boiling point of 165° C. under 0.3 mbar were obtained, corresponding to a yield of 75% based on p-methoxybenzaldehyde dimethyl acetal.

We claim:

1. A process for preparing a 3-arylacrylic acid or its derivative of the formula I

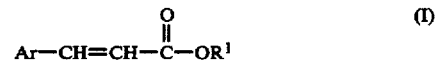

where
Ar is aryl which has one or more substituents which do not react with ketene and are stable under the conditions of the reaction described below, and
$R^1$ is hydrogen, an alkali metal, an alkaline earth metal, ammonium or $C_1$–$C_{20}$-alkyl,
which comprises a first stage in which a dialkyl acetal of an aromatic aldehyde of the formula II

where $R^2$ is $C_1$–$C_4$-alkyl, is reacted with ketene of the formula $CH_2$=C=O in the presence of catalytic amounts of a protic or Lewis acid to give a 3-arylpropionic acid derivative of the formula III

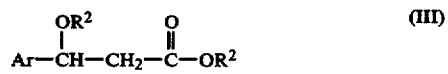

and a second stage in which this intermediate III is reacted in the presence of acid or base and, in the case where $R^1$ is $C_1$–$C_{20}$-alkyl, additionally with a $C_1$–$C_{20}$-alkanol to give the final product I.

2. A process as claimed in claim 1, which is used to prepare a 3-arylacrylic acid or its derivative I, where
Ar is phenyl, biphenylyl or naphthyl, each of which is substituted by one to three $C_1$–$C_4$-alkyl groups, $C_1$–$C_4$-alkoxy groups, hydroxyl groups, phenoxy groups, amino groups which can be mono-or disubstituted by $C_1$–$C_4$-alkyl, halogen atoms, nitro groups or a methylenedioxy group, wherein the substituents are identical or different.

3. A process as claimed in claim 1, which is carried out without isolation of the intermediate III.

4. A process as claimed in claim 1 for preparing a 3-arylacrylic acid or its derivative I, which comprises reacting a 3-arylpropionic acid derivative III in the presence of acid or base and, in the case where $R^1$ is $C_1$–$C_{20}$-alkyl additionally with a $C_1$–$C_{20}$-alkanol.

5. A process as claimed in claim 1, wherein said substituent is a $C_1$–$C_4$-alkoxy group.

* * * * *

UNITED STATES PATENT AND TRADEMARK OFFICE
CERTIFICATE OF CORRECTION

PATENT NO. : 5,359,122
DATED : October 25, 1994
INVENTOR(S) : Michael HUELLMANN, et al.

It is certified that error appears in the above-indentified patent and that said Letters Patent is hereby corrected as shown below:

On the title page, Item [75], the third inventor's residence is spelled incorrectly. It should read:

--Bad Duerkheim--

Signed and Sealed this

Fourteenth Day of March, 1995

Attest:

BRUCE LEHMAN

Attesting Officer

Commissioner of Patents and Trademarks